US00PP21711P3

(12) United States Plant Patent
Biringer

(10) Patent No.: US PP21,711 P3
(45) Date of Patent: Feb. 15, 2011

(54) KATSURA TREE NAMED 'BIRINGER'

(50) Latin Name: *Cercidiphyllum japonicum*
Varietal Denomination: Biringer

(75) Inventor: Josef Biringer, Mt. Vernon, WA (US)

(73) Assignee: Biringer Nursery LP, Mt. Vernon, WA (US)

( * ) Notice: Subject to any disclaimer, the term of this patent is extended or adjusted under 35 U.S.C. 154(b) by 9 days.

(21) Appl. No.: 12/454,943

(22) Filed: May 26, 2009

(65) Prior Publication Data

US 2010/0306890 P1 Dec. 2, 2010

(51) Int. Cl.
*A01H 5/00* (2006.01)

(52) U.S. Cl. ..... Plt./216

(58) Field of Classification Search ..... Plt./216
See application file for complete search history.

*Primary Examiner*—Kent L Bell
(74) *Attorney, Agent, or Firm*—Michelle Bos

(57) ABSTRACT

'Biringer' Katsura is a newly and distinct variety of Katsura tree (*Cercidiphyllum japonicum*) having characteristics that are of commercial value in the nursery trade. As compared to Common Katsura, 'Biringer' Katsura has darker green summer foliage; narrower, more upright branch angles; a tendency to hold the leaves later in the autumn; and greater winter hardiness.

5 Drawing Sheets

Genus and species: *Cercidiphyllum japonicum.*
Variety denomination: 'Biringer'.

BACKGROUND OF THE NEW VARIETY

The inventor discovered a single unusual tree in a row of Katsura trees at his commercial nursery in Mount Vernon, Wash. in July 2003. This unusual tree, believed to be a naturally occurring whole-plant mutation of Common Katsura, exhibited narrower, more upright branch angles and darker green foliage than the surrounding Common Katsura trees (not patented). This single tree was marked and observed during the remainder of 2003 and through 2004. In August 2004, 200 to 300 trees were propagated by chip budding and by cuttings (mist propagation). The propagated trees were planted in 2005. All trees from this propagation appeared identical to the original tree. Since 2005, approximately 500 trees have been propagated from the second-generation trees, and all are identical, confirming the trueness to type of the new variety. The new Katsura tree has been given the name 'Biringer'.

BRIEF SUMMARY OF THE INVENTION

The distinguishing characteristics of the 'Biringer' Katsura as compared to Common Katsura are as follows:

1. Narrower, more upright growth habit.
2. Less vigor, by approximately 25-30%.
3. Darker green summer foliage.
4. Delayed senescence of leaves in the autumn, retaining foliage approximately two weeks longer.
5. Greater winter hardiness.

DETAILED BOTANICAL DESCRIPTION

The Common Katsura tree, *Cercidiphyllum japonicum*, Siebold and Zucc. ex J.Hoffm. and H. Schult., is described in *Hortus Third* (MacMillan) as follows: Upright-branching tree to 100 ft., trunk often branched above the base; leaves orbicular to ovate, to 4 in. long and cordate, crenate-serrate, glabrous, dark green above, glaucescent beneath, becoming yellow or scarlet in autumn; flowers before leaves; follicles about ¾ in. long.

The detailed description which follows documents the differences between the Common Katsura tree and the claimed 'Biringer' Katsura tree. This description was prepared from observation and sampling of two year old trees at Mount Vernon, Skagit County, Wash. in October 2008. Certain characteristics of this variety, such as growth and color, may change with changing environmental conditions, e.g., photoperiod, temperature, moisture, soil conditions, nutrient availability, or other factors. Color descriptions and other terminology are used in accordance with their ordinary dictionary descriptions unless the context clearly indicates otherwise. Color designations (hue/value/chroma) are made with reference to the Munsell Book of Color, Kollmorgen Instruments Corp., 405 Little Britain Road, New Windsor, New York 12553.

Tree

Figure 1:
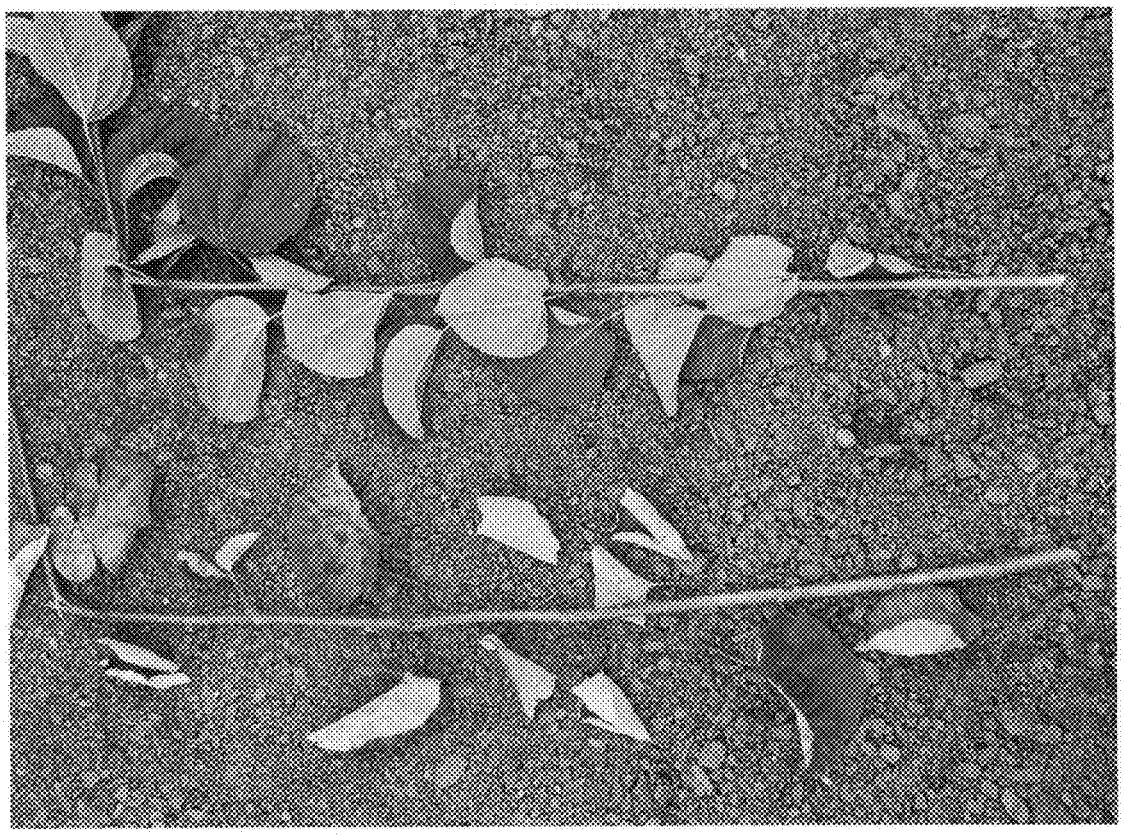
FIG. 1 One-year shoots of Katsura, showing difference in senescence between 'Biringer' Katsura (top) and Common Katsura (bottom).
Figure 2:
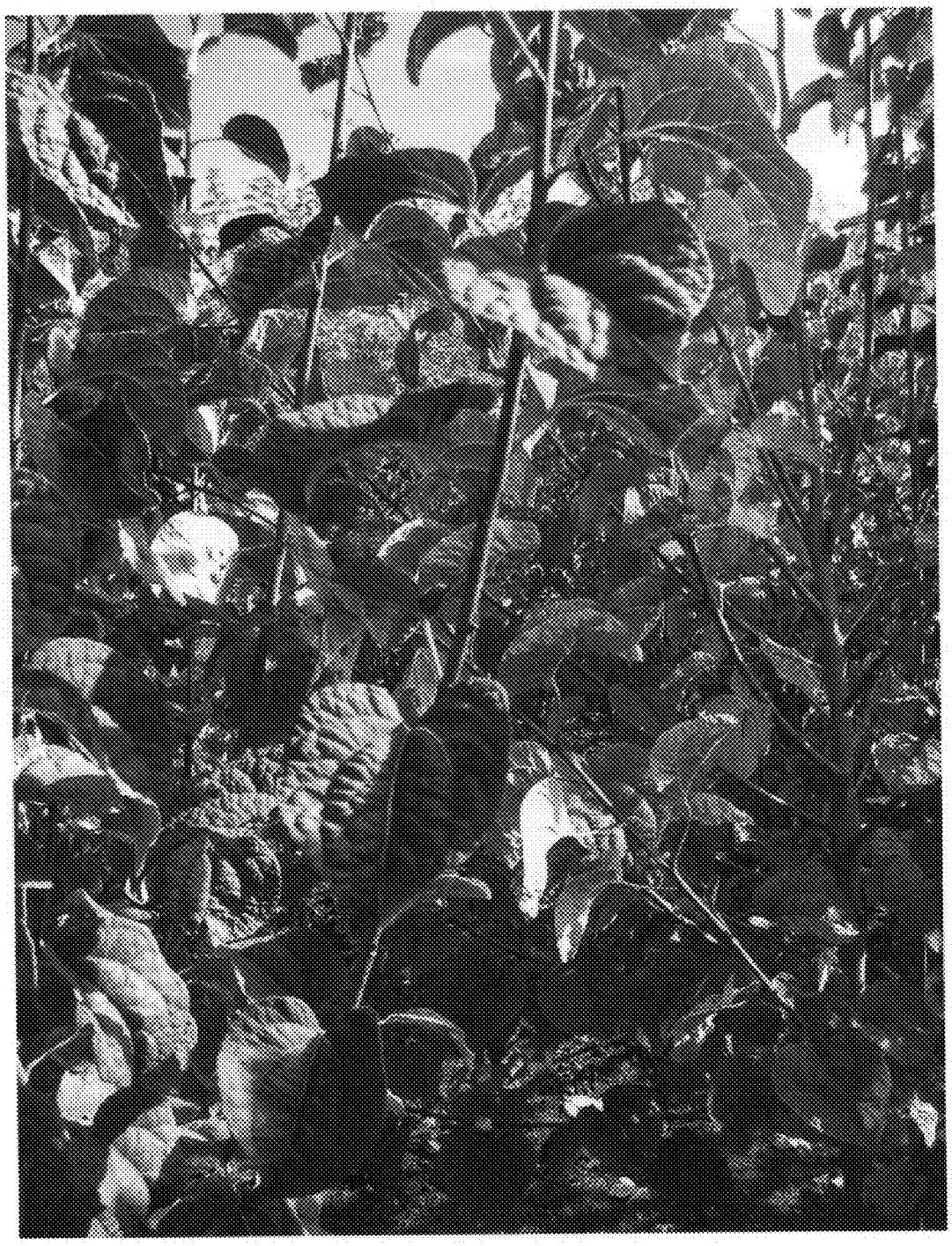
FIG. 2 Two-year old Katsura trees in nursery row. 'Biringer' Katsura is in the foreground on the left; Common Katsura is on the right.
Figure 3:
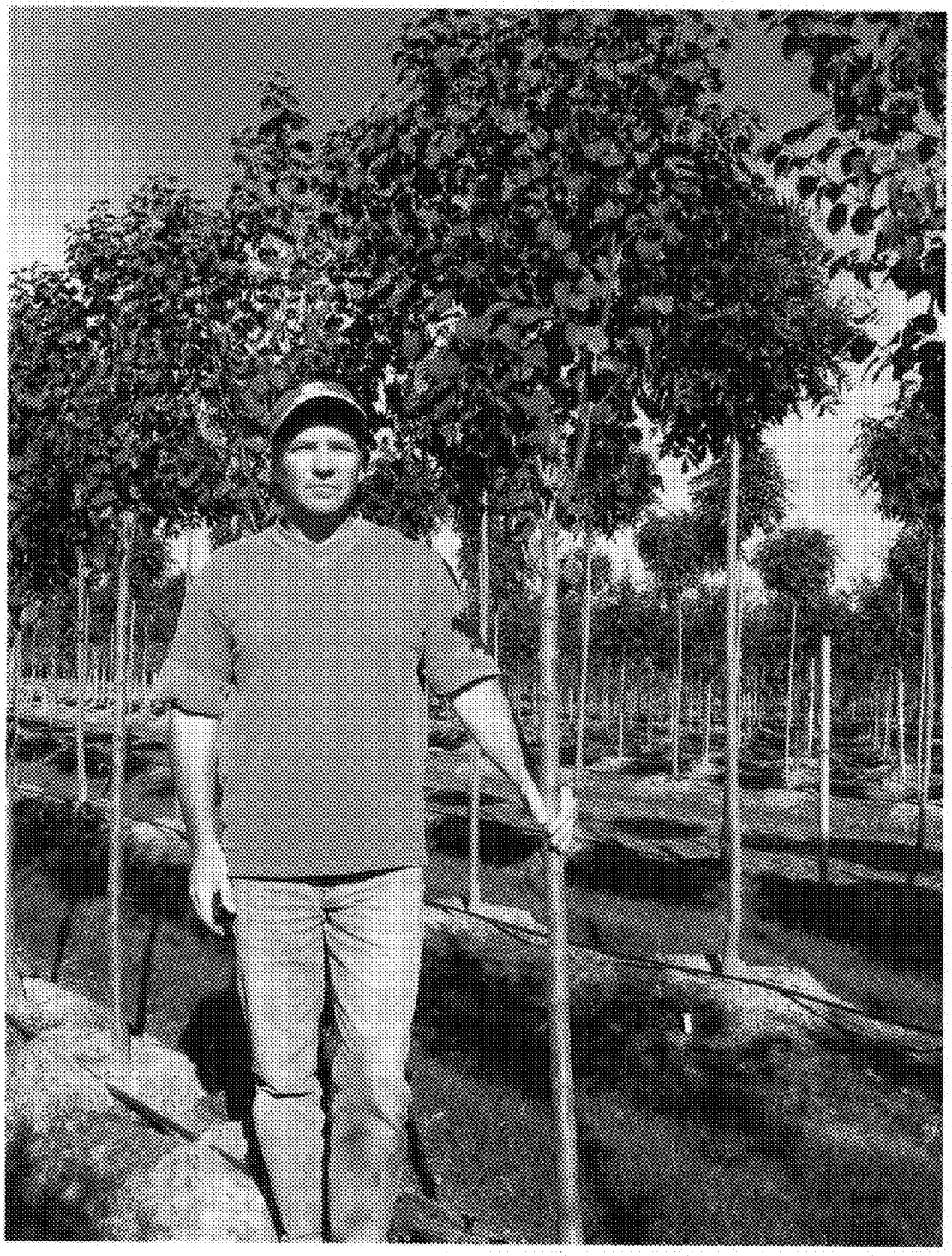
FIG. 3 Three year old 'Biringer' Katsura trees in nursery row.
Figure 4:
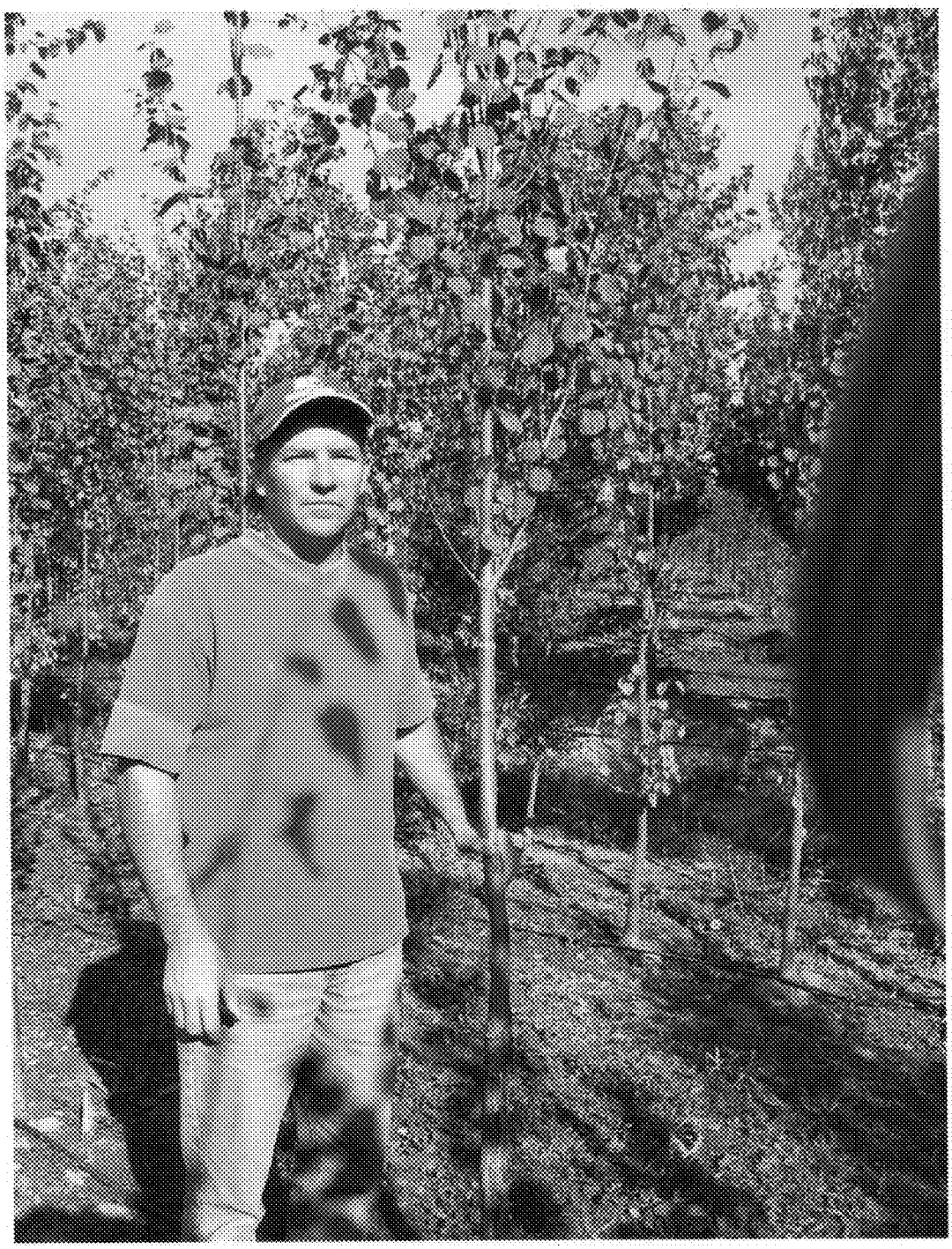
FIG. 4 Three year old Common Katsura trees in nursery row.
Figure 5:
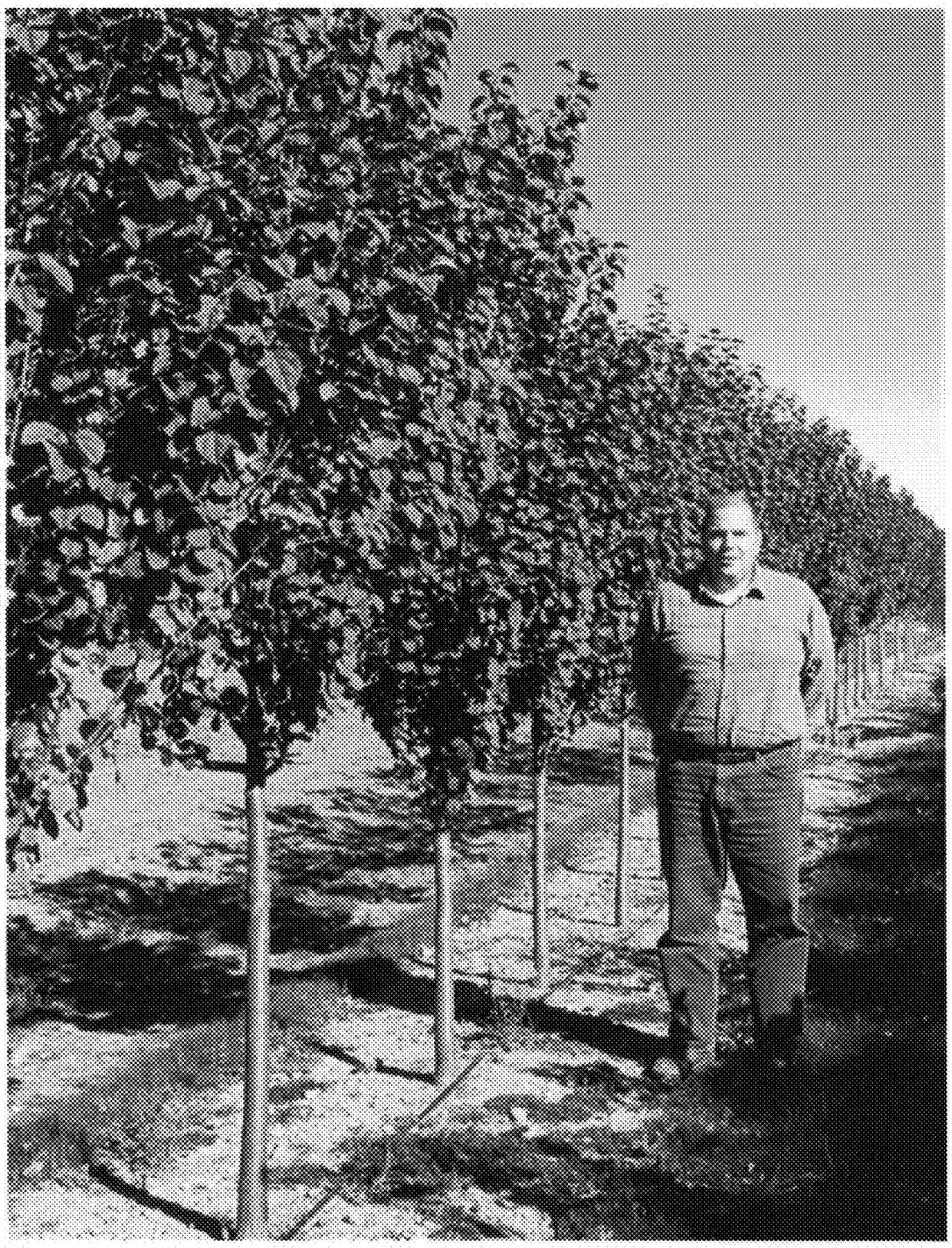
FIG. 5 Four year old 'Biringer' Katsura trees in nursery row.

*Height.*—Similar to that of Common Katsura, approximately 5 feet at end of first season in the nursery (FIG. 2).

*Width.*—First year 12 to 18 inches at the widest point, approximately 6 inches narrower than Common Katsura.

*Overall shape.*—Upright branching tree. 'Biringer' has more upright growth habit and reduced vigor compared to Common Katsura, thus appearing more compact.

Trunk

*Texture.*—Smooth.

*Color.*—Medium brown, (7.5 YR 5/4). No difference in trunk bark texture or color from that of Common Katsura.

Branches

*Habit.*—Upright branching, with side branches averaging 30 degrees from the vertical, compared to 45 degrees from the vertical in Common Katsura.

*Size.*—About 60 to 90 cm long, and about 8 to 10 mm in diameter at the base; Somewhat more slender and with about 30% less vigor than Common Katsura.

*Color.*—Olive brown, (2.5 Y 4/4), as compared to light brown (10 R 4/4) in Common Katsura.

*Lenticels.*—Round to oblong, inconspicuous, light tan (7.5 YR 6/2), less than 1 mm in length and diameter.

*Internode length.*—5.5 cm, as compared to 6.0 cm in Common Katsura.

Leaves

Based on observation of 10 leaves on Oct. 11, 2008.

*Size.*—6.5 cm long and 6.5 cm wide, similar to Common Katsura.

*Form.*—Orbicular to ovate, apex acuminate, base cordate; similar to Common Katsura.

*Texture.*—Upper surface glabrous; lower surface glaucescent.

*Color.*—Dark green (2.5 G 3/4) above, lighter green (2.5 G 6/8) beneath. Upper surface of leaves on Common Katsura, when sampled, were more yellowish (2.5 GY 4/4), showing signs of senescence.

*Marginal form.*—Crenate and glabrous above, glaucescent beneath, similar to that of Common Katsura.

*Petiole.*—2.7 cm in length, 2 mm in width, color reddish (2.5 R 3/10), as compared to a more purple color (2.5 R 3/4) in Common Katsura.

Flowers

*Blossoms.*—No flowers have been observed. The inventor has not observed flowers on Katsura trees. The literature suggests that Katsura trees typically produce separate male and female flowers in spring before foliation.

*Seeds.*—None observed.

Other Distinguishing Characteristics

*Hardiness.*—On Nov. 20, 2006, a low temperature of 12 degrees Fahrenheit was reached in an area where Common and 'Biringer' Katsura trees were growing. By the following spring it was observed that more than 50% of the Common Katsura trees died, while all of the sixty plants of 'Biringer' cv. of the same age survived undamaged.

*Disease/insect resistance and susceptibility.*—No observable difference in adaptability to various soil conditions, disease and insect infestation, or fall coloring have been observed between 'Biringer' Katsura and Common Katsura.

I claim:

1. A new and distinct variety of Katsura tree named 'Biringer' as herein described and illustrated.

* * * * *